US008119078B2

(12) United States Patent
Rogers et al.

(10) Patent No.: US 8,119,078 B2
(45) Date of Patent: Feb. 21, 2012

(54) SYSTEM FOR STABILIZING GAS HYDRATES AT LOW PRESSURES

(75) Inventors: Rudy E. Rogers, Starkville, MS (US); Guochang Zhang, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 620 days.

(21) Appl. No.: 12/284,018

(22) Filed: Sep. 17, 2008

(65) Prior Publication Data

US 2009/0098028 A1 Apr. 16, 2009

Related U.S. Application Data

(60) Provisional application No. 60/994,087, filed on Sep. 17, 2007.

(51) Int. Cl.

| | |
|---|---|
| ***B01J 3/00*** | (2006.01) |
| *B01J 19/00* | (2006.01) |
| *C07C 9/00* | (2006.01) |

(52) U.S. Cl. ........... 422/242; 422/129; 422/198; 585/15

(58) Field of Classification Search .................. 422/129, 422/162, 242, 198; 585/15
See application file for complete search history.

(56) References Cited

U.S. PATENT DOCUMENTS

| | | | | |
|---|---|---|---|---|
| 6,389,820 | B1 * | 5/2002 | Rogers et al. | 62/45.1 |
| 6,653,516 | B1 * | 11/2003 | Yoshikawa et al. | 585/15 |
| 7,781,627 | B2 * | 8/2010 | Woo et al. | 585/15 |
| 2008/0072495 | A1 * | 3/2008 | Waycuilis | 48/190 |

* cited by examiner

*Primary Examiner* — Walter D Griffin
*Assistant Examiner* — Natasha Young
(74) *Attorney, Agent, or Firm* — Lawrence Arthur Schemmel

(57) ABSTRACT

The present invention provides a system for stabilizing gas and particularly gas hydrates at low pressures and for safe storage and transportation of the gas. The invention also provides minimization of the decomposition of the gas in hydrate form.

18 Claims, 7 Drawing Sheets

| Run# | $V_{wl}$ | $C_{sds}$ | $V_{total}$ | $M_g$ | $M_{gh}$ | 12 min dissociation | | Long term dissociation | | | $N_e$ | $V_{g/gh}$ |
|---|---|---|---|---|---|---|---|---|---|---|---|---|
| | (ml) | (PPM) | (L) | (gram) | (gram) | Volume, L | percentage,% | Volume, L | percentage,% | $T_d^*$, H | | |
| 1 | 300 | 300 | 60.061 | 40.071359 | 340.07136 | 0.002 | 0.003329948 | 0.29 | 0.482842444 | 24 | 6.65479 | 149.747 |
| 2 | 300 | 300 | 62.174 | 41.481106 | 341.48111 | 0.002 | 0.003216779 | 0.003 | 0.004825168 | 24 | 6.4286296 | 154.376 |

FIG. 4

| Run# | $V_{wl}$ (ml) | $C_{sds}$ (PPM) | $V_{total}$ (L) | $M_g$ (gram) | $M_{gh}$ (gram) | 12 min dissociation | | Long term dissociation | | | $N_e$ | $V_{g/gh}$ |
|---|---|---|---|---|---|---|---|---|---|---|---|---|
| | | | | | | Volume, L | percentage,% | Volume, L | percentage,% | $T_d^*$, H | | |
| 1 | 250 | 1000 | 57.287 | 42.9026 | 292.903 | 0.002 | 0.003491193 | 0.009 | 0.015710371 | 24 | 5.8142 | 171.2993378 |
| 2 | 250 | 1000 | 54.875 | 41.0963 | 291.096 | 0.001 | 0.001822323 | 0.002 | 0.003644647 | 24 | 6.06976 | 165.1052084 |
| 3 | 250 | 1000 | 54.59 | 40.8828 | 290.883 | 0.001 | 0.001831837 | 0.001 | 0.001831837 | 24 | 6.10145 | 164.3682329 |
| 4 | 250 | 600 | 56.39 | 42.2309 | 292.231 | 0.001 | 0.001773364 | 0.004 | 0.007093456 | 85 | 5.90669 | 169.0047432 |
| 5 | 250 | 600 | 56.629 | 42.4099 | 292.41 | 0.028 | 0.049444631 | 0.042 | 0.074166946 | 48 | 5.88176 | 169.6171538 |
| 6 | 300 | 1000 | 62.188 | 46.573 | 346.573 | 0.013 | 0.020904355 | 0.03 | 0.048240818 | 24 | 6.42718 | 157.1573553 |
| 7 | 300 | 1000 | 61.017 | 45.6961 | 345.696 | 0.069 | 0.113083239 | 0.122 | 0.199944278 | 25.3 | 6.55053 | 154.5892558 |
| 8 | 250 | 1000 | 49.62 | 37.1608 | 287.161 | 0.079 | 0.159209996 | 0.036 | 0.072551391 | 24 | 8.05509 | 151.3402827 |
| 9 | 250 | 1000 | 56.232 | 42.1125 | 292.113 | 0.05 | 0.088917342 | 0.03 | 0.053350405 | 24 | 7.10794 | 168.5994739 |

FIG. 5

| Run# | $V_{wl}$ (ml) | $V_{inj.}$ (ml) | $C_{sds}$ (PPM) | $V_{total}$ (L) | $M_g$ (gram) | $M_{gh}$ (gram) | 12 min dissociation Volume, L | 12 min dissociation percentage,% | Long term dissociation Volume, L | Long term dissociation percentage,% | $T_d^*$, H | $N_e$ | $V_{g/gh}$ |
|---|---|---|---|---|---|---|---|---|---|---|---|---|---|
| 1 | 150 | 100 | 1000 | 45.086 | 33.7652 | 283.765 | 0.001 | 0.002217983 | 0.002 | 0.004435967 | 24 | 7.38762 | 139.157 |
| 2 | 180 | 100 | 1000 | 47.31 | 35.4308 | 315.431 | 0.001 | 0.002113718 | 0.018 | 0.038046925 | 256 | 7.88517 | 131.363 |
| 3 | 250 | 100 | 1000 | 65.608 | 49.1343 | 399.134 | 0.392 | 0.597488111 | 0.524 | 0.798683087 | 48 | 7.10751 | 143.966 |
| 4 | 250 | 80 | 600 | 56 | 41.9388 | 371.939 | 0.097 | 0.173214286 | 0.114 | 0.203571429 | 24 | 7.85112 | 131.868 |
| 5 | 250 | 5 | 600 | 56.67 | 42.4406 | 297.441 | 0.021 | 0.037056644 | 0.034 | 0.059996471 | 24 | 5.99505 | 166.869 |
| 6 | 250 | 40 | 600 | 55.614 | 41.6497 | 331.65 | 0.062 | 0.11148272 | 0.07 | 0.125867587 | 6.4 | 6.94736 | 146.868 |

FIG. 6

SYSTEM FOR STABILIZING GAS HYDRATES AT LOW PRESSURES

CROSS-REFERENCE TO RELATED APPLICATION

This application claims priority from U.S. Provisional Patent Application Ser. No. 60/994,087 filed Sep. 17, 2007. The entirety of that provisional application is incorporated herein by reference.

FIELD OF THE INVENTION

The present invention relates to a system for stabilizing gas, more specifically, for stabilizing gas in a hydrate form at pressures safe for storing and transporting said gas while minimizing the decomposition of the hydrate form.

BACKGROUND OF THE INVENTION

Description of Prior Art

Natural gas can be stored by various means including compressed gas storage, liquified gas storage, underground storage, and adsorption. Types of such natural gas or any of its components include gas compositions composed primarily of methane but may also contain other components such as ethane, propane, isobutane, butane, $CO_2$, and/or nitrogen. However, current gas storage means have potential problems and deficiencies, namely that liquified gas storage is expensive and involves safety hazards such as possible tank rupture. Natural gas can be stored underground but that method is limited to porous sandstone formations and salt domes or other areas having satisfactory geological features that are typically located in non-populated areas. As a result, gas must be transported to populated areas to be used. Compressed gas storage is likewise expensive and is also hazardous due to high pressures required for storage.

Gas hydrates are crystalline inclusion compounds that are formed when water and a certain gas are mixed under elevated pressures and reduced temperatures. Gas hydrates are a subset of the class of solid compounds called clathrates. Clathrates have molecules of one type of compound completely enclosed within the crystalline structure of molecules of another type of compound. Clathrates have been considered in efforts to devise alternative methods for storing and transporting natural gas. For gas hydrates, host water molecules form a lattice structure that resemble a cage through hydrogen bonding. A guest molecule is contained within the cage-like crystalline structure of the host water molecules. The guest can be natural gas and/or its components.

Commercial applications of optimized means for forming and storing and/or transporting natural gas in gas hydrates can be quite expansive: (1) transportation of natural gas in competition with LNG; (2) above-ground storage of natural gas for peak-load use by electric power plants; (3) capture and transportation of stranded gas where no pipelines exist; (4) small-scale needs for use and storage of natural gas, e.g., emergency supplies for hospitals or rural needs; (5) storage and transportation of ultradeepwater gas production; (6) capture, storage, and transportation of eventual methane produced from vast offshore gas hydrate deposits; and (7) storage of gas unloaded at LNG terminals. This process can possibly be utilized for storage of natural gas to be used as an alternative for gasoline in commercial and in municipal truck and bus fleets. Natural gas is typically compressed and requires pressure of about 3500 psi that adds excessive weight to the container and increases safety concerns.

Although many of the technical hurdles traditionally associated with hydrate formation have been overcome, specifically by U.S. Pat. No. 6,389,820, efforts to stabilize gas hydrates under conditions safe for storage and transportation (i.e., 1 atmosphere or atm) have been largely unsuccessful to date. In cores containing natural gas hydrates, Ershov and Yakushev found that a remnant of hydrates persisted for a long time after lowering confining pressures to 1 atm. After one year in this work, the temperature was raised and, as the temperature approached the normal ice melting point, all remnants of hydrate quickly melted. However, 90% of the original hydrate had dissociated soon after lowering confining pressure to 1 atm. (Ershov, E. D. and Yakushev, V. S., "Experimental Research on Gas Hydrate Decomposition in Frozen Rocks," *Cold Regions Science and Technology,* 20, 147-156 (1992). Ershov, et al. found that some final fraction of hydrate less than 10% can persist for more than a year but dissociates rapidly as the temperature T approaches the ice melting point.

An initially high dissociation rate of methane gas-hydrates (Structure I or sI) shortly after reducing confining hydrate pressure to 1 atm in the optimum temperature range has been consistently discussed in other papers, while realizing fairly stable dissociation rates after initial decompositions. But no other researcher reports achieving stability of natural gas hydrates (Structure II or sII) at any time when pressure is lowered in the optimum temperature range. (Circone, S., Stern, L. A., and Kirby, S. H., "The Effect of Elevated Methane Pressure on Methane Hydrate Dissociation," *American Mineralogist,* 89, 1192-1201 (2004). Circone, et al. stated that the rate of gas evolution changed over time and that in the first hour after rapid depressurization, the initial dissociation rate was high and then decreased to progressively slower rates.

Another group reported similar rapid dissociation rates for methane hydrates within minutes of reducing confining pressure to 1 atm in the optimum temperature range, but that group observed very slow decomposition rates thereafter. (Takeya, S., Shimada, W., Kamata, Y., Ebinuma, T., Uchida, T., Nagao, J., and Narita, H., "In-Situ X-ray Diffraction Measurements of the Self-Preservation Effect of $CH_4$ Hydrate," *J. Phys. Chem. A.,* 105, 9756-9759 (2001). Takeya, et al. determined that the initial dissociation rate was very fast within the first several tens of minutes and then became relatively slow.

Methane hydrates are sI structures. Although the hydrate composition may be predominantly methane, natural-gas hydrates containing propane form sII structures. Many industrial applications that would involve storage and/or transportation of natural gas would form sII structures. Therefore, capability to achieve stable hydrates with either methane or natural gas would be a significant process advantage.

In the process described by Circone, et al., at least half of the methane hydrate sample decomposed immediately upon reducing pressure above the sample to 1 atm. The natural gas hydrate all dissipated quickly after lowering the pressure to 1 atm while maintaining the optimum stable temperature range. (Circone, et al.). Circone, et al. determined that 90-100% of a 30 g sample dissociated in a few minutes to a few hours at both low and high T and in the intermediate T range at least half of the sample persisted for a few hours to several tens of hours.

Other processes fail to demonstrate natural-gas hydrate stability (i.e., Structure II hydrates formed from methane-rich gases having some propane or i-butane) in the stability window of −5° C. to −10° C. (Circone, et al.). Circone, et al.

determined that temperature-dependent dissociation behavior appeared to be unique to methane hydrate. $CO_2$ hydrate, also sI, did not show any of the temperature-dependent behavior below 273 K, while an sII methane-rich hydrate showed no anomalous preservation at 268 K.

Based on the prior art and its deficiencies, there exists a clear need for a system of stabilizing gas in both the sI and sII hydrate forms at lower pressures to safely transport and store gas hydrates. The present invention provides such a system.

SUMMARY OF THE INVENTION

This invention provides a practical, economically viable, and safe means for stabilizing gases in sI and sII hydrate forms. One object of the invention is to provide a means for stabilizing gases (and also minimizing the decomposition), such as natural gas and its components, in a gas hydrate form so that the gases can be stored and transported at pressures and temperatures that are considered safe by industry standards. In accordance with the present invention as described herein, a method and system for storing gases is provided that comprises forming and stabilizing gas hydrates in the presence of a water-surfactant solution.

Some advantages of this new process, system, and/or apparatus include, but are not limited to, the following: (1) liquefied natural gas can be expensive and liquefied natural gas plants typically have high capital costs and must be built at large gas fields to justify the cost. The system of the present invention to store natural gas at 1 atm may service smaller gas fields economically; (2) storage conditions for the storage system and process disclosed herein are less stringent than liquefied natural gas from the standpoint of temperature and pressure storage; (3) liquefied natural gas storage near populated areas or docking facilities may raise serious safety concerns and potential fire and explosion risks. The gas hydrate system of the present invention is safe since, in a simplistic view, the gas is encased in ice. Gas from gas hydrate is released only after transfer of heat to decompose the solid water host structure. In an era of terrorist threats, this safety issue becomes critical; (4) other gas hydrate processes that may be stable at 1 atm have little if any potential to be economical on a large scale. Other ultrastable gas hydrate processes involve the slow conversion of ice to hydrates. The system and process of the present invention provides a rapid means to generate stable hydrates; (5) the system and process of the present invention provides a product that is stable upon the initial release of pressure after forming the hydrates. State-of-the-art processes have perhaps a 50% or so decomposition and release of their stored gases. Although their remaining gases may be stably sequestered, the 50% or so decomposition loss cannot be tolerated for any viable commercial use due to the economics of such loss; and (6) the system and process of the present invention is economical and fast and has the potential of being utilized for storing gases economically on a large scale.

With the foregoing and other objects, features, and advantages of the present invention that will become apparent hereinafter, the nature of the invention may be more clearly understood by reference to the following detailed description of the preferred embodiments of the invention and to the appended claims.

BRIEF DESCRIPTION OF THE DRAWINGS

These drawings accompany the detailed description of the invention and are intended to illustrate further the invention and its advantages:

FIG. 4 is a table showing data values from the Example 0.1 process.

FIG. 5 is a table showing data values from the Example 2 process.

FIG. 6 is a table showing data values from the Example 3 process.

DETAILED DESCRIPTION OF THE INVENTION

The present invention provides for a process, system, and apparatus for stabilizing gases, more specifically, for stabilizing gases in a hydrate form at pressures that are safe for storing and for transporting the gases. Additional advantages of the invention provide for minimalization of the decomposition of the hydrate form. It will be understood by those skilled in the art that the present invention is not limited in its application to the details of the arrangements described herein since it is capable of other embodiments and modifications. Moreover, the terminology used herein is for the purpose of such description and not of limitation. The phrase "hydrate formation" and its equivalents refer to the nucleation, growth, and/or the agglomeration of gas in hydrate form. The term "biosurfactant" refers to a specific group of surfactants, particularly microbially-produced surfactants.

Figure 7:
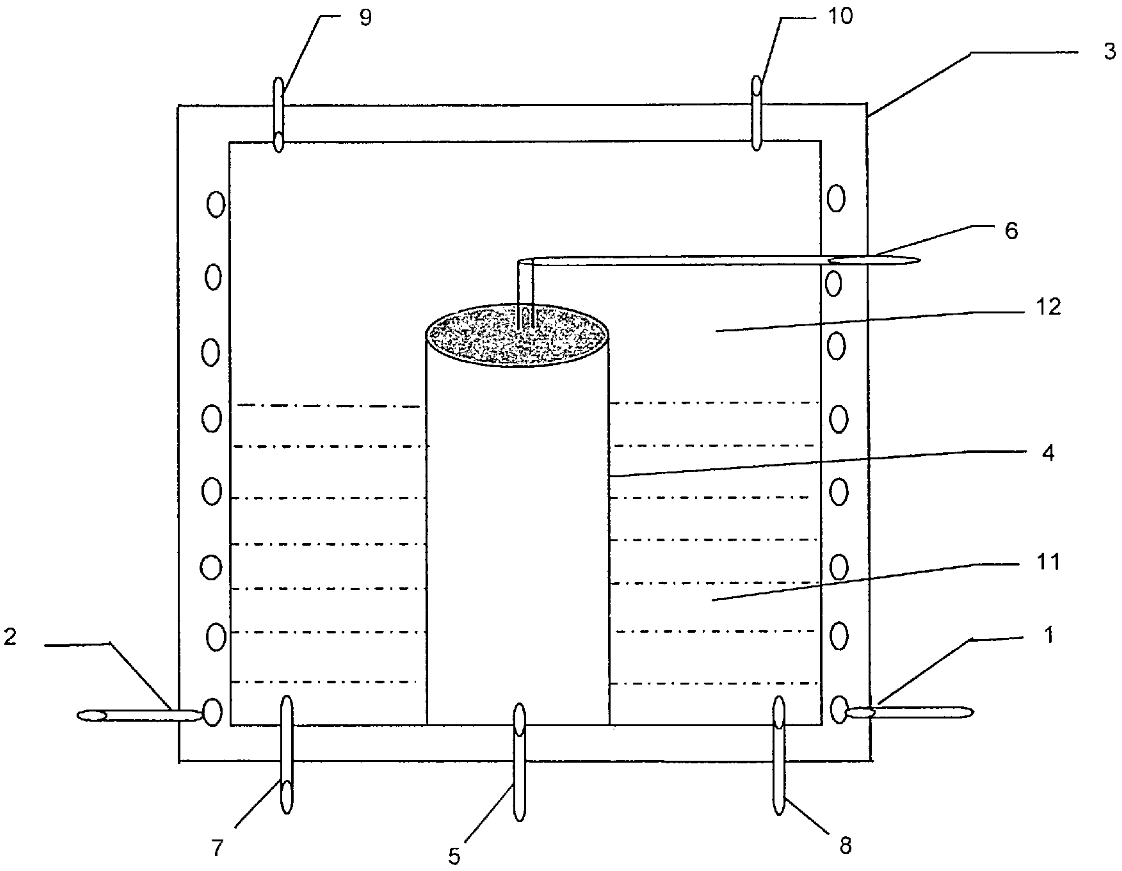
FIG. 7 is a pictorial representation of the system and method of the invention.

Gas Stabilization Process:

Step 1—Forming Gas Hydrates. FIG. 7 is a pictorial representation of the system and method of the present invention showing each feature thereof. A water-surfactant-gas system is made by first combining water and surfactant (FIG. 7) to an appropriate concentration level. Once formed, this surfactant solution is pumped into an appropriate hydrate formation container which must be constructed of materials having strength and thickness and heat conductivity properties for a maximum process control of both temperature and pressure so that temperature and/or pressure can be increased and/or decreased independently or simultaneously, if necessary. Secondly, the appropriate gas constituent is injected into the container which is under pressure. Suitable hydrate-forming hydrocarbon constituents include, but are not limited to, methane, ethane, propane, butane, isobutane, neopentane, ethylene, propylene, isobutylene, cyclopropane, cyclobutane, and mixtures thereof Suitable hydrate-forming non-hydrocarbon constituents include, but are not limited to, carbon dioxide, sulfur dioxide, nitrogen oxides, hydrogen sulfide and mixtures thereof Gas hydrates will form rapidly. The present invention is applicable to gas-water mixtures where hydrates can form including, preferably, to natural gas and its components. This particular step is known in the art, particularly as disclosed in U.S. Pat. No. 6,389,820.

Step 2—Forming Additional Gas Hydrates. Additional hydrates can be formed from interstitial water that remains in the formation container after Step 1 is completed. These additional hydrates can be preferably created by either increasing the internal pressure of the container or decreasing the internal temperature of the container or vessel. Additional hydrates can be created by increasing or decreasing the pressure and/or temperature of the container independently or simultaneously, as required. An external means, such as that described in Component 4 herein, is preferably used to lower the temperature of the container.

Step 3—Adding Additional Surfactant and Water. It has been determined that upon formation of gas hydrates according to the aforementioned procedure, tiny fractures can result throughout the mass of hydrates that comprise the section of the container. Consequently, these cracks serve as a means by which the entire system of packed hydrates can become destabilized and decompose. Therefore, this step of the process and system of the present invention adds an appropriate/effective amount of surfactant solution, water and surfactant, in order for the fractures to be filled with the additional solution. The appropriate/effective amount of surfactant solution is determined such that it optimizes stability of the hydrate formation. In order to optimize the stability of the hydrate formation, Step 3 may not be necessary or may need to be performed one or more times.

The surfactants used in the present invention include biosurfactants, anionic surfactants and mixtures thereof. The surfactants may include, but are not limited to: alkyl sulfates, alkyl ether sulfates, alkyl sulfonates, alkyl aryl sulfonates, sodium lauryl sulfate, and sodium dodecyl sulfate. Suitable surfactants solubilize the gas utilized and adsorb on metal.

Step 4—Decreasing the Pressure. Once the additional hydrates have been formed, this new stabilized mass of gas hydrates can sustain pressure decreases while minimizing decomposition. Therefore, the internal pressure of the vessel is lowered to a range considered industrially safe for storage and transportation, which is approximately 1 atm.

Gas Stabilization Apparatus:

Component 1—A container/vessel for holding a mixture of water and surfactant, and at least one hydrate-forming constituent under pressure. The container must be constructed of materials having strength, thickness, and heat conductivity properties for a maximum process control of both temperature and pressure so that temperature and/or pressure can be increased and/or decreased independently or simultaneously, if necessary. The container should be preferably structured for batch, continuous, or semi-continuous operation. The container materials may include, but are not limited to, stainless steel or a titanium hull. It should be understood by one skilled in the art that the optimized container size and materials may vary depending on the specific application, cost, etc. Component 2—A first inlet for adding water and surfactant to said container under Pressure. This inlet provides a means by which water and surfactant can be added to the aforementioned container. The addition of water and surfactant can be accomplished according to Step 1 and/or Step 2 in the aforementioned process. Component 3—A second inlet for adding at least one hydrate-forming constituent to said Container under pressure. The addition of the gas component is required to form the hydrates according to Step 1 in the aforementioned process. Component 4—At least one coolant means for cooling said mixture to below a temperature where, at least some of said water and surfactant, and at least one hydrate-forming constituent within said container combine to form a solid hydrate. For example, inside the lower half of the container tubing may be positioned through which cooling water is circulated having a sufficient amount of ethylene glycol or other depressant or coolant to depress the freezing point of the water. Component 5—At least one heat transfer means for conducting latent heat away from the high pressure vessel during said formation of the solid hydrate. This heat transfer means is required to (a) uniformly and rapidly remove the latent heat to form hydrates from natural gas and (b) to add latent heat to the system at the time of desired decomposition of the stored gas hydrates. The heat transfer means should be composed, completely or in part, of at least one thermally conductive material such as aluminum, copper, or other material of similar thermal conductivity. Furthermore, the heat transfer means must provide an appropriate amount of surface area and configuration to adsorb and support hydrates formed from the gas with the aid of the surfactant. The heat transfer means or exchanger must be constructed of materials having sufficient strength, thickness, and heat conductivity properties for a maximum process control of both temperature and pressure. Finally, the heat transfer means must provide a configuration of the heat transfer means that provides a symmetrical buildup of hydrates on the heat transfer means or exchanger to allow free gas movement until the container under pressure becomes full of hydrates.

In a preferred embodiment of the present invention, the design of the heat transfer means or exchange means preferably includes U-tubes having at least one inlet and at least one outlet for coolant flow. The U-tubes are preferably attached or welded to a tube sheet which is secured to a top domed-flange header. The header in the dome appropriately directs coolant flow into the U-tube inlet or outlet.

In another embodiment, stainless steel fins are preferably attached or resistance-welded onto the U-tubes. Preferably aluminum, stainless steel, and copper (and any alloys thereof) are considered viable materials for the U-tubes and/or the fins. However, other conductive materials may be appropriate depending upon cost, size, or type of hydrate formation, etc.

Further, in another embodiment of the present invention, a total heat transfer area would be composed of heat-exchanger tubes, fins, and walls of the pressure vessel. Component 6—At least one outlet for depressurizing said container under pressure in order to destabilize the stored gas hydrates for utilization of the gas.

The present invention is described via the detailed examples herein which are presented by way of illustration and are not to be limiting in scope.

EXAMPLE 1

Figure 1:
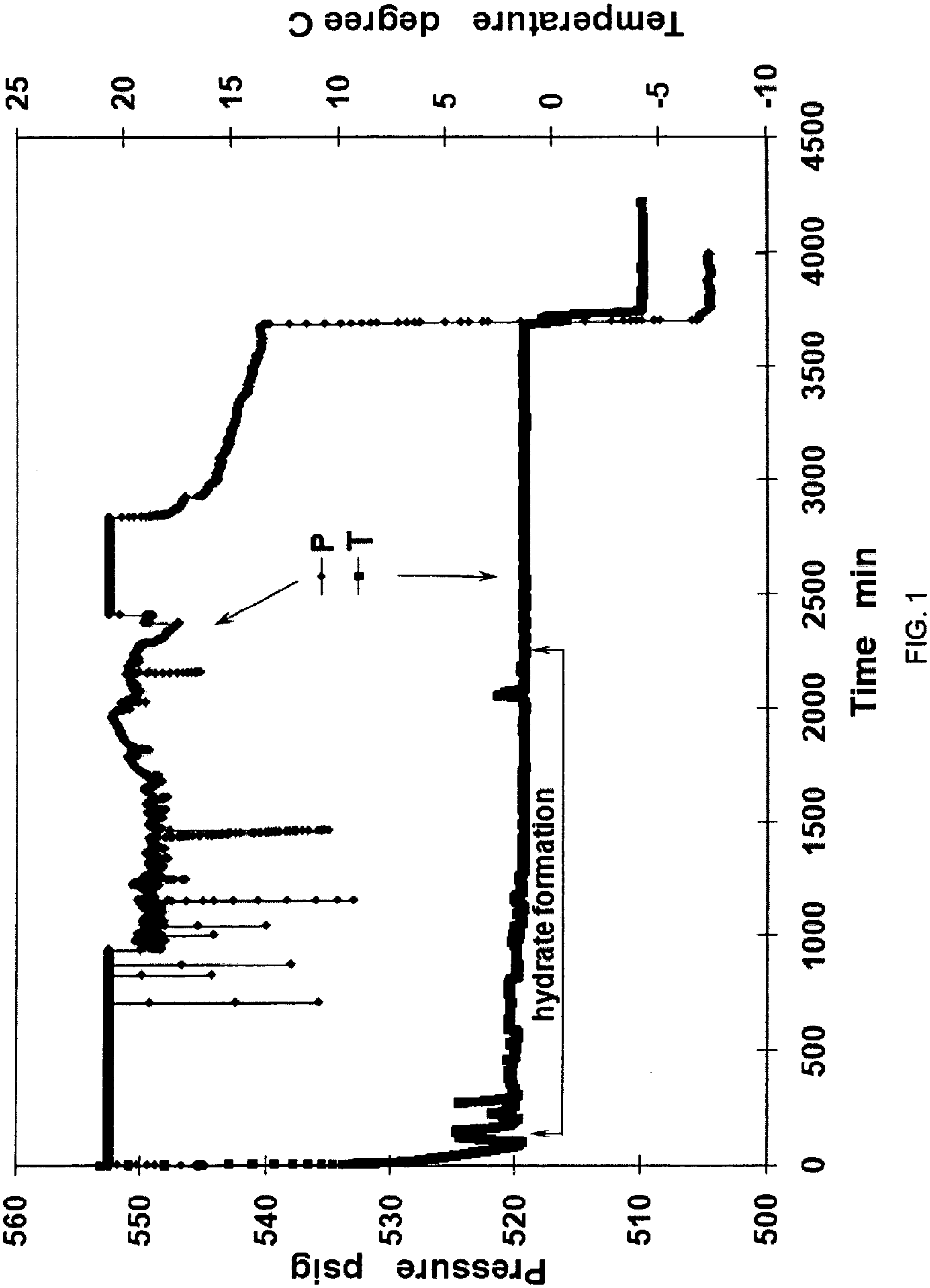
FIG. 1 shows a graph of temperature and pressure of methane hydrate formation by the process of Example 1.

In preparation of methane hydrates, a 1-inch diameter aluminum (Al) pipe of 5.5 inch length (1 inch diameter) was placed in the center of the 500 mL test cell. Methane hydrates were generated from 300 ml of 300 PPM sodium dodecyl sulfate (SDS) distilled water solution at +0.5° C. and under constant pressure of 3.84 MPa methane. After hydrate formation, methane hydrates were cooled down to −5.0° C. Upon depressurization to one atm in 5 seconds, methane hydrates exhibited great stability below −1.0° C. both during and after depressurization. The evolutions of pressure and temperature during hydrate formation are shown in FIG. 1. FIG. 4 is a table showing data values from the Example 1 process.

FIG. 1 defines the pressure-temperature-time parameters for the formation of methane gas-hydrates that exhibit ultra-stability when pressure is lowered to 1 atm for storage or transportation. The pressure (P) and temperature (T) traces as a function of time reflect the step sequences in the formation procedures outlined in Example 1. The spikes in the pressure trace reflect action of the constant pressure regulator to maintain constant pressure on the system. Gas pressure in the test cell drops as gas absorbs into the gas-hydrate solid solution, necessitating the addition of more gas to maintain constant pressure. The upward spikes of the temperature trace reflect when hydrates form and release latent heat of formation. Toward the end of the graph (right side), the temperature trace declines rapidly when the temperature of the system is manually lowered to −5° C. and the pressure trace follows as gas in the test cell cools without replenishment. An aluminum cylinder in the test cell helped to rapidly dissipate latent formation heats and to collect hydrates.

FIG. 4 shows stability data of methane hydrates at −5.0° C. and 1 atmosphere, where:

$V_{w1}$=volume of the SDS distilled water solution added to the test cell at the beginning, in ml;

$C_{sds}$=concentration of SDS in distilled water, in PPM;

$V_{total}$=total volume of gas recovered from the gas hydrates, in liter(s), (at 20° C. and 1 atm);

$T_d$=Time of gas hydrate dissociation performed at one atm and −5.0° C., in hour(s);

*=Monitoring stopped; stability goes beyond this time; $M_g$=Mass of gas recovered from solid hydrates, in g (calculated with Peng-Robinson equation of state);

$M_{gh}$=Mass of solid gas hydrates=mass of gas and SDS distilled water solution, in g;

$N_e$=hydrate number=mole number ratio of water to gas occluded in hydrates;

Methane=99.5% methane gas; and $V_{g/gh}$=volume of gases occluded in per volume of hydrates (at STP).

EXAMPLE 2

During the formation of natural gas hydrates, a 1-inch diameter copper (Cu) pipe or solid Cu cylinder of 5.5 inches length was placed in the center of the 500 mL test cell. Natural gas hydrates were created in two steps. In the first step, 250 ml of SDS distilled water solution was added to the test cell and hydrates were produced at +0.5° C. under constant pressure of 3.84 MPa natural gas consisting of 90% methane, 6% ethane, and 4% propane. In the second step, when cooled to −1.5° C. at the same constant pressure of 3.84 MPa, natural gas hydrates grew again from the remaining free water. Thereafter, when hydrate formation was completed in the second step, hydrates were cooled down to −5.0° C. Upon depressurization to one atmosphere in 5 seconds, natural gas hydrates exhibited great stability below −1.0° C. both during and after depressurization. Variation of pressure and temperature during hydrate formation is given in FIG. 2. FIG. 5 is a table showing data values from the Example 2 process.

Figure 2:
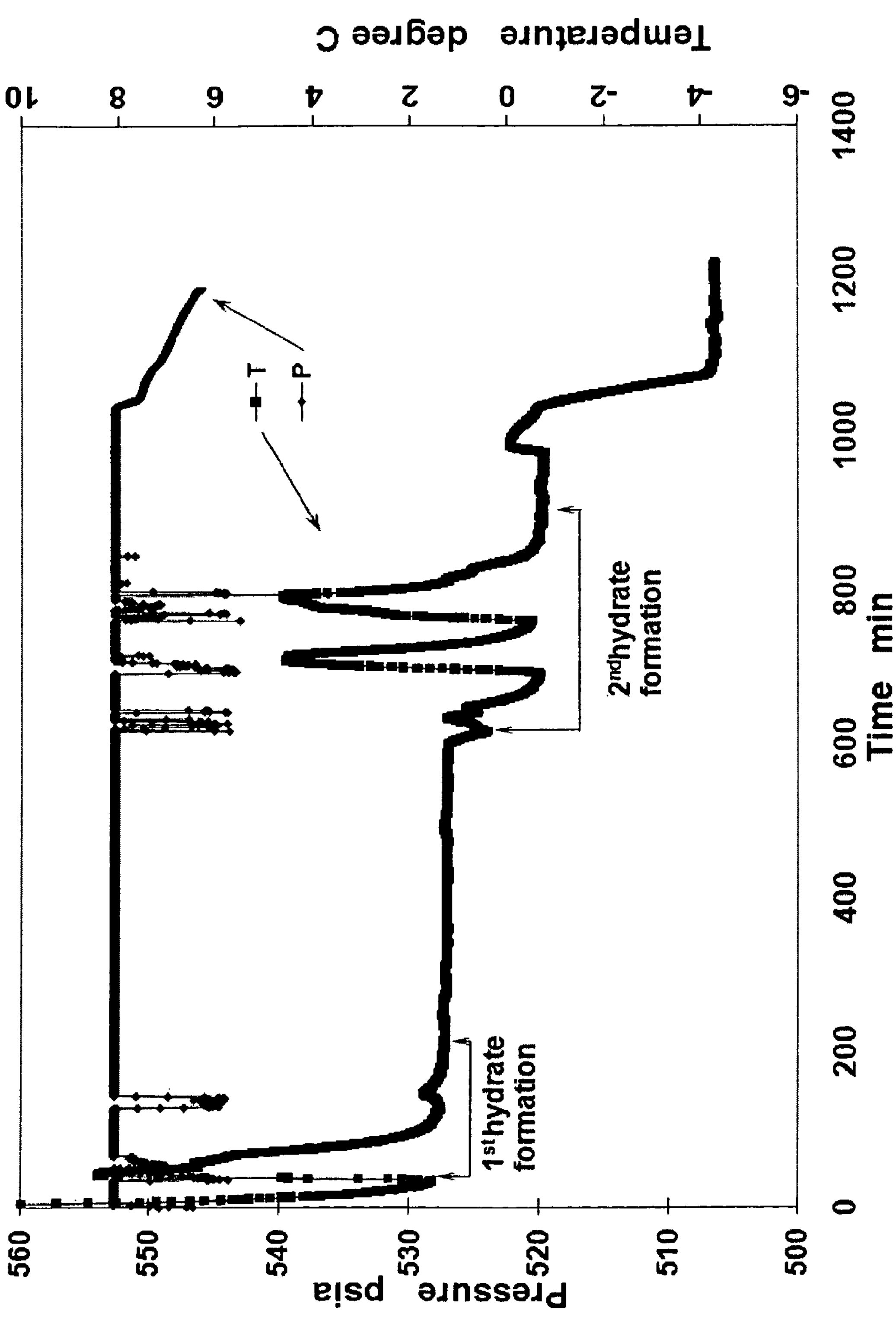
FIG. 2 shows a graph of temperature and pressure of natural gas hydrate formation by the process of Example 2.

FIG. 2 defines the pressure-temperature-time parameters for the formation of natural gas gas-hydrates that exhibit ultra-stability when pressure is lowered to 1 atm for storage or transportation. The P and T traces as a function of time reflect the step sequences in the formation procedures outlined in Example 2. The spikes in the pressure trace reflect action of the constant pressure regulator to maintain constant pressure on the system. The "2$^{nd}$ hydrate formation" noted on the graph marks the manual lowering of system temperature to −1.5° C. from the +0.5° C. of the "1$^{st}$ hydrate formation." A series of spikes occurred also in the pressure trace upon this temperature lowering as the constant pressure regulator admitted gas to the test cell to replenish gas going into hydrate solid-solution. At about 1000+ minutes, temperature was finally lowered to −5° C.; no more free water existed to form hydrates and the gas pressure decreased without more gas added as gas temperature declined to −5° C. A copper cylinder in the test cell helped to rapidly dissipate latent formation heats and to collect hydrates.

FIG. 5 shows stability data of natural gas hydrates at −5.0° C. and 1 atmosphere, where:

$V_{w1}$=volume of the SDS distilled water solution added to the test cell at the beginning, in ml;

$C_{sds}$=concentration of SDS in distilled water, in PPM;

$V_{total}$=total volume of gas recovered from the gas hydrates, in liter(s), (at 20° C. and 1 atm);

$T_d$=Time of gas hydrate dissociation performed at one atm and −5.0° C., in hour(s);

*=Monitoring stopped; stability goes beyond this time;

$N_e$=hydrate number=mole number ratio of water to gas occluded in hydrates;

$M_g$=Mass of gas recovered from solid hydrates, in g (calculated with Peng-Robinson equation of state);

$M_{gh}$=Mass of solid gas hydrates=mass of gas and SDS distilled water solution, in g;

Natural gas=90% methane, 6% ethane, and 4% propane; and $V_{g/gh}$=volumes of gases occluded in per volume of hydrates (at STP).

EXAMPLE 3

Figure 3:
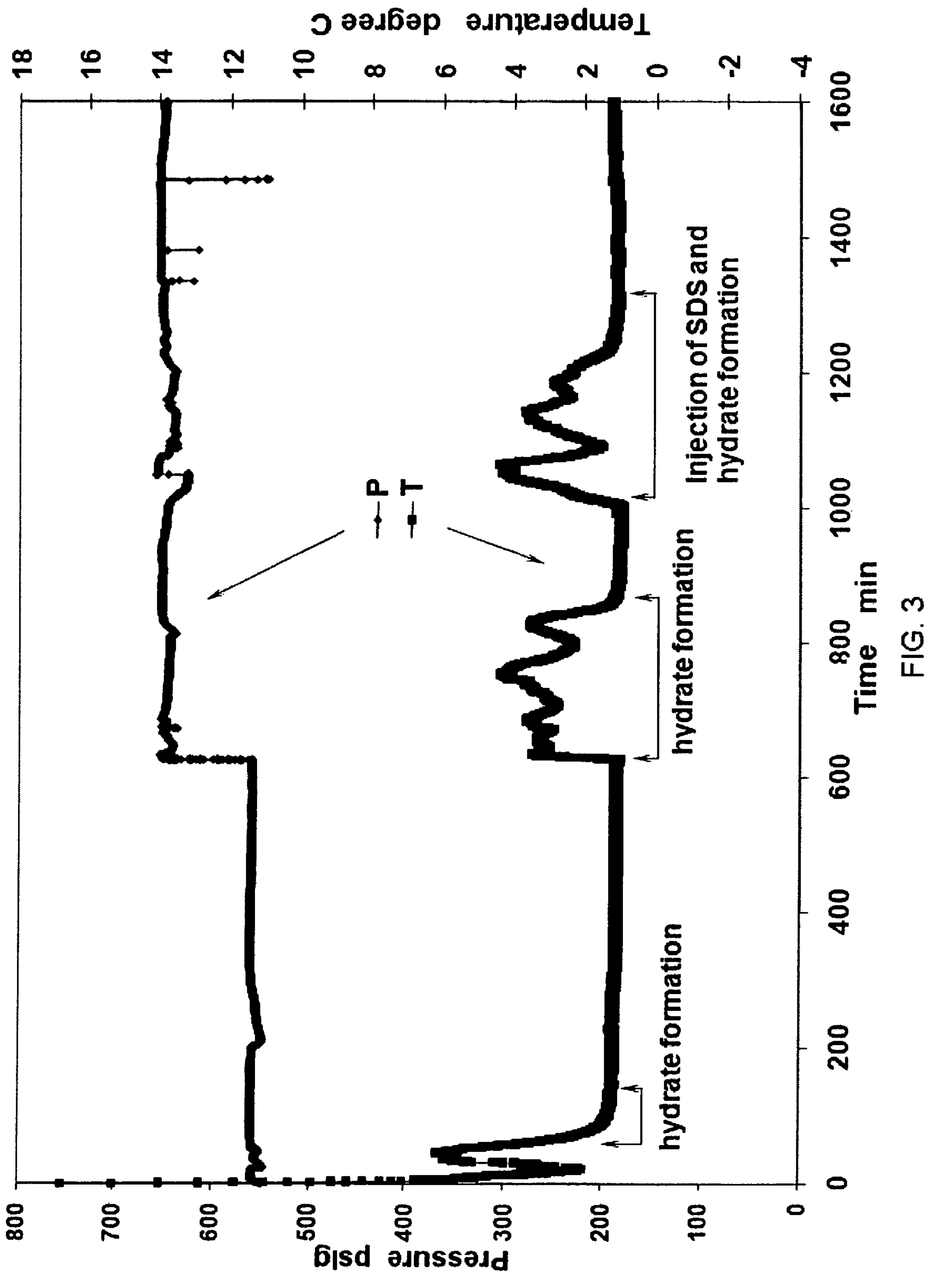
FIG. 3 shows a graph of temperature and pressure of natural gas hydrate formation by the process of Example 3.

During the formation of natural gas hydrates, a 1-inch diameter Cu pipe of 5.5 inches length was placed in the center of the 500 mL test cell. Next, 250 ml of SDS solution was added to the test cell. At first, natural gas hydrates were created under a constant temperature of +0.5° C. and a constant pressure of 3.84 MPa. Then, secondly the pressure inside the test cell was increased to 4.53 MPa to react the remaining free water into hydrates. When hydrate formation was finished, an SDS solution of up to 100 ml was injected into the test cell to form gas hydrates again at +0.5° C. and 4.53 MPa. After additional hydrate formation, methane hydrates were cooled down to −5.0° C. Upon depressurization to one atm in 5 seconds, natural gas hydrates demonstrated great stability below −1.0° C. FIG. 3 shows the record of pressure and temperature during hydrate formation. FIG. 6 is a table showing data values from the Example 3 process.

FIG. 3 defines the pressure-temperature-time parameters for the formation of natural gas gas-hydrates that exhibit ultra-stability when pressure is lowered to 1 atm for storage or transportation. The P and T traces as a function of time reflect the step sequences in the formation procedures outlined in Example 3. Peaks in the temperature trace show periods of high hydrate formation. The 2$^{nd}$ set of T peaks denoting hydrate formation occurs upon increasing test cell pressure. The 3$^{rd}$ set of T peaks occurs upon adding more SDS-water solution to the test cell. A copper pipe in the test cell helped to rapidly dissipate latent formation heats and to collect hydrates.

FIG. 6 shows additional stability data of natural gas hydrates at −5.0° C. and 1 atmosphere, where:

$V_{w1}$=volume of the SDS distilled water solution added to the test cell at the beginning, in ml;

$C_{sds}$=concentration of SDS in distilled water, in PPM;

$V_{total}$=total volume of gas recovered from the gas hydrates, in liter(s), (at 20° C. and 1 atm);

$T_d$=Time of gas hydrate dissociation performed at one atm and −5.0° C., in hour(s);

*=Monitoring stopped; stability goes beyond this time;

$N_e$=hydrate number=mole number ratio of water to gas occluded in hydrates;

$M_g$=Mass of gas recovered from solid hydrates, in g (calculated with Peng-Robinson equation of state);

$M_{gh}$=Mass of solid gas hydrates=mass of gas and SDS distilled water solution, in g;

Natural gas=90% methane, 6% ethane, and 4% propane; and $V_{g/gh}$=volumes of gases occluded in per volume of hydrates (at STP).

This disclosure has for the first time described and fully characterized a system for stabilizing gas and particularly gas hydrates at low pressures and for safe storage and transportation of the gas and a system for minimizing the decomposition of the gas in hydrate form. The above detailed description is presented to enable any person skilled in the art to make and use the invention. Specific details have been disclosed to provide a comprehensive understanding of the present invention and are used for explanation of the information provided. These specific details, however, are not required to practice the invention, as is apparent to one of ordinary skill in the art. Descriptions of specific applications are meant to serve only as representative examples. Various suitable changes, modifications, combinations, and equivalents to the preferred embodiments may be readily apparent to one skilled in the art and the general principles defined herein may be applicable to other embodiments and applications while still remaining within the spirit and scope of the invention. The claims and specification should not be construed to unduly narrow the complete scope of protection to which the present invention is entitled. It should also be understood that the figures are presented for example purposes only. No intention exists for the present invention to be limited to the embodiments shown and the invention is to be accorded the widest possible scope consistent with the principles and features disclosed herein.

What is claimed is:

1. A method for stabilizing gas hydrates, comprising:

forming gas hydrates from a mixture of water, surfactant, and at least one hydrate-forming gas constituent in a container under pressure;

forming additional gas hydrates by increasing the internal pressure of said container under pressure, decreasing the internal temperature of said container under pressure, or a combination thereof;

forming the gas hydrates on the surface of a thermally conductive material for providing effective heat transfer and for further providing a symmetrical formation of the gas hydrates and effective adsorption and stability support of the gas hydrates;

optionally adding to said container under pressure an effective amount of additional water and surfactant for filling any crack or fracture throughout the mass of gas hydrates formed to further increase and optimize the stability of the gas hydrate formation; and rapidly decreasing within about five seconds after the gas hydrates have been formed the internal pressure of said container under pressure until a pressure for safely storing and transporting the gas hydrates is reached.

2. The method of claim 1, wherein the surfactant is a biosurfactant.

3. The method of claim 1, wherein the surfactant is an anionic surfactant.

4. The method of claim 3, wherein the anionic surfactant is selected from the group consisting of alkyl sulfates, alkyl ether sulfates, alkyl sulfonates, and alkyl aryl sulfonates.

5. The method of claim 4, wherein the anionic surfactant is an alkyl sulfate.

6. The method of claim 5, wherein the alkyl sulfate is sodium lauryl sulfate.

7. The method of claim 5, wherein the alkyl sulfate is sodium dodecyl sulfate.

8. The method of claim 1, wherein the at least one hydrate-forming gas constituent is a hydrocarbon gas, a non-hydrocarbon gas, or a combination thereof.

9. The method of claim 8, wherein the hydrocarbon gas is selected from the group consisting of methane, ethane, propane, butane, isobutane, neopentane, ethylene, propylene, isobutylene, cyclopropane, cyclobutane, and mixtures thereof.

10. The method of claim 8, wherein the non-hydrocarbon gas is selected from the group consisting of carbon dioxide, sulfur dioxide, nitrogen, hydrogen sulfide, and mixtures thereof.

11. The method of claim 1, further comprising:

forming additional gas hydrates by increasing the internal pressure of said container under pressure and decreasing the internal temperature of said container under pressure.

12. The method of claim 1, further comprising, after the hydrates have been formed, rapidly decreasing within about five seconds after the gas hydrates have been formed the internal pressure of the container under pressure and maintaining the internal pressure at about 1 atmosphere and decreasing the internal temperature of the container under pressure and maintaining the internal temperature at from about −1° C. to about −5° C. for safely storing and transporting the gas hydrates and for increasing the stability of the gas hydrates.

13. A system for stabilizing gas hydrates, the system Comprising:

a container under pressure;

a first inlet for adding water and surfactant to said container under pressure;

a second inlet for adding said at least one hydrate-forming constituent to said container under pressure;

at least one coolant means for cooling said water, surfactant, and at least one hydrate-forming constituent below a temperature where at least some of said water, surfactant, and at least one hydrate-forming constituent within said container under pressure combine to form a solid hydrate;

at least one heat transfer means for rapidly conducting latent heat away from the container under pressure during said formation of a solid hydrate, wherein the heat transfer means provides for a symmetrical formation of hydrates thereon and also provides compatible adsorption surfaces for the surfactant-assisted adsorption and support of the solid hydrates; and at least one outlet for depressurizing said container under pressure.

14. The system of claim 13, wherein the container under pressure is a metal container.

15. The system of claim 14, wherein the metal container is stainless steel.

16. The system of claim 14, wherein the metal container is titanium.

17. The system of claim 13, wherein the at least one heat transfer means further provides compatible surfaces for the symmetrical buildup of the solid hydrates for permitting free gas movement until the container under pressure becomes full of the solid hydrates.

18. The system of claim 13, wherein the at least one heat transfer means comprises at least one thermally conductive material.

* * * * *